United States Patent [19]
Buffard et al.

[11] Patent Number: 5,209,568
[45] Date of Patent: May 11, 1993

[54] MACHINE FOR MONITORING THE CHARACTERISTICS OF MATERIALS EXHIBITING A PHASE TRANSFORMATION, REVERSIBLE OR OTHERWISE

[75] Inventors: Laurent Buffard, Saint Cyr Sur Mer; Michel Raymond, La Ciotat; Renee-Paule Girones; Eric Weynant, both of Cadenet, all of France

[73] Assignee: Imago, Ajaccio, France

[21] Appl. No.: 769,231

[22] Filed: Oct. 1, 1991

[30] Foreign Application Priority Data

Oct. 9, 1990 [FR] France .................... 90 12765

[51] Int. Cl.$^5$ ............................................. G01N 3/18
[52] U.S. Cl. ............................................. 374/49; 374/45
[58] Field of Search ............ 374/43, 45, 46, 49, 374/50, 51, 55, 56, 142, 143, 208; 73/801, 818, 826

[56] References Cited

U.S. PATENT DOCUMENTS

| | | | |
|---|---|---|---|
| 1,888,755 | 11/1932 | Barr | 374/49 |
| 2,154,280 | 4/1939 | Nadai et al. | 374/49 |
| 2,347,661 | 5/1944 | Butland | 374/43 |
| 2,375,032 | 5/1945 | Parke et al. | 374/50 |
| 2,375,034 | 5/1945 | Semchysen | 374/50 |
| 2,904,993 | 9/1959 | Grover et al. | 374/49 |
| 2,942,455 | 6/1960 | Smith | 374/50 |
| 3,803,365 | 4/1974 | Cartier | 374/49 X |
| 4,019,365 | 4/1977 | Woo | 374/46 |
| 4,837,776 | 6/1989 | Poll | 374/51 X |

FOREIGN PATENT DOCUMENTS

| | | |
|---|---|---|
| 1434553 | 4/1965 | France . |
| 2633050 | 12/1989 | France . |
| 60-230034 | 11/1985 | Japan .................... 374/49 |
| 2220270 | 1/1990 | United Kingdom . |

OTHER PUBLICATIONS

"Acoustic Emission Test Facility," *The Review of Scientific Instruments*, vol. 4, No. 8, Darrell R. James and Steve H. Carpenter, Aug. 1971.

Gogotsi et al, "Device for Investigations into Strength and Deformability of Refractory Material at High Temperatures", Industrial Laboratory, vol. 41, No. 6, Jun. 1975, pp. 941–943.

*Primary Examiner*—William A. Cuchlinski, Jr.
*Assistant Examiner*—G. Bradley Bennett
*Attorney, Agent, or Firm*—Oliff & Berridge

[57] ABSTRACT

This machine comprises a thermally insulated enclosure, with which are associated a control unit, a temperature source, a device for making the temperature uniform, a specimen holder disposed inside the enclosure and measurement units, means being provided for mounting the various control or monitoring components fixed to the enclosure, whilst permitting the thermal expansions of the enclosure due to temperature differences.

Application to the monitoring of components made of shape-memory alloys.

15 Claims, 4 Drawing Sheets

FIG.1

FIG_2

FIG_5

FIG.3

FIG_4

MACHINE FOR MONITORING THE CHARACTERISTICS OF MATERIALS EXHIBITING A PHASE TRANSFORMATION, REVERSIBLE OR OTHERWISE

BACKGROUND OF THE INVENTION

The subject of the present invention is a machine for monitoring the characteristics of materials exhibiting a phase transformation, reversible or otherwise.

This machine is intended especially for monitoring components made of shape-memory alloys which exhibit a martensitic transformation, but also other materials such as ceramics or polymers.

DESCRIPTION OF THE PRIOR ART

Shape-memory alloys are transformed from a high temperature phase to a low temperature phase on passing to a defined temperature. It is from this transformation that the shape-memory alloys derive their shape-memory properties. From these properties, it turns out that any object made of a shape-memory alloy may be given two shapes: one at low temperature and the other at high temperature.

This transformation is also sensitive to the mechanical stresses applied to the material: the more the stress is increased the more the transformation temperature rises.

It is important therefore to be able to measure a stress or a deformation on these alloys or to verify the uniformity of the characteristics of components made of shape-memory alloys. These mechanical deformation measurements may be advantageously supplemented by measurements of other parameters characteristic of the martensitic transformation, such as the electrical resistivity and the acoustic emission.

Currently machines which are suitable for carrying out such measurements, do not exist, these machines appearing difficult to construct in order to give reliable results over a wide range of temperatures of the order of −150° C. to +300° C., taking into account the problems of expansions, of thermal stresses and of temperature withstanding ability of the various measurement instruments.

SUMMARY OF THE INVENTION

The object of the invention is to provide a machine capable of subjecting at least one specimen to a stress, or to a given deformation over a wide range of temperatures, for example from −150° C. to +300° C., and of measuring especially the force exerted on these specimens, the deformation of the specimens, the temperature of the specimens as well as, optionally, other parameters such as electrical resistivity and acoustic emission.

For this purpose, the machine in question comprises a thermally insulated enclosure, with which are associated a control unit, a temperature source, a device for making the temperature uniform, a specimen holder disposed inside the enclosure and measurement units, means being provided for mounting the various control or monitoring components fixed to the enclosure, whilst permitting the thermal expansions of the enclosure due to temperature differences.

As a result it is important to ensure a high withstanding ability of these components without affecting the expansion phenomena.

According to an embodiment of this machine, the thermally insulated enclosure comprises a steel vessel of generally cylindrical shape comprising ends curved outwardly which is housed inside a metal casing, with rigid insulating material in between, one of the ends of the vessel being equipped, on the one hand, with tubular inlets traversing, loosely, the insulation of the casing and which are intended respectively for supplying cryogenic fluid, for the passage of a drive shaft of a fan for circulating gaseous fluid inside the enclosure and making the temperature uniform and regulating the pressure inside the enclosure, these three tubular inlets also being fixed to a stirrup-shaped part integral with a ring fixed to the cylindrical portion of the vessel in the vicinity of this end and, on the other hand, with at least one radial opening for the passage of a specimen holder and of the measurement instrumentation, each opening being delimited by a collar, the various collars being integral with a ring which surrounds the vessel and which is connected by means of longitudinal bars to a second ring which is mounted in a fitted manner and with the capability for sliding axially over the ring carrying the stirrup.

This structure with rings and linking bars enables the various components to be solidly mounted with perfect positioning, which does not affect the expansion phenomena, taking into account the capabilities for sliding of the two rings mounted so as to fit one inside the other.

Advantageously, the vessel has a horizontal axis, its casing rests on a support and it comprises two diametrical openings for the passage of the instrumentation, of which a portion is itself fixed to the support.

The vessel and the structure with which it is associated rest on the insulating material and have only one point, fixed in relation to the outside, formed by the passage of the instrumentation.

According to another characteristic of this machine, the thermal enclosure comprises a cylindrical wall made of thin metal sheet which, extending in the cylindrical portion of the vessel, inside the latter, and delimiting a central zone and an annular zone, comprises openings for the passage of the specimens and of tee instrumentation, the fan being disposed facing the central zone, the end opposite that on the side where the fan is located being equipped with a flux separator encouraging the return of the air via the annular zone, a heating resistance element being disposed in the central zone, downstream from the fan, in the outflow direction of the flux of air.

A temperature probe, disposed downstream from the fan and from the resistance element, is connected to the regulator which controls the temperature source. If it is required to heat, the regulator controls the operation of the resistance element. On the contrary, if it is required to cool, the regulator controls the injection of cryogenic fluid via a calibrated nozzle from a proportional solenoid valve.

The fan improves:
- the heat transfer between the heating resistance element and the air of the enclosure,
- the mixing of the cryogenic and gaseous fluids, especially the evaporation of the cryogenic fluid,
- the heat transfer between the gaseous fluid of the enclosure and the specimens.

In the end of the vessel, opposite that traversed by the shaft of the fan, a safety valve is mounted limiting the internal pressure to values of slight over-pressure of 1.1 to 1.2 bar.

According to another characteristic of the invention, the collar integral with the vessel and turned upwards is extended by a tubular portion which, traversing the insulation and the outer casing, is equipped, outside the latter, with a platform on which is mounted a hoisting device intended for moving the instrumentation and the specimens during their installation in the vessel and their withdrawal out of the latter.

Advantageously, the hoisting device comprises a gear motor driving an endless screw, of axis parallel to that of the instrumentation, on which is mounted a nut integral with a carriage which, guided on rails parallel to the screw, is locked in terms of translational movement onto the support frame carrying the instrumentation, inductive sensors being provided for controlling the stopping of the motor at the end of the travel up and the travel down of the carriage.

The support frame carrying the instrumentation is equipped with a stirrup which, in the measurement position, is inside the vessel and serves for the mounting of each component to be monitored, by bearing or by fixing the extremity of the latter opposite the side on which the hoisting device is located, the other extremity of each component bearing against or fixed to the extremity of a rod of orientation generally radial in relation to the enclosure, mounted in a sliding manner in relation to the support frame and whose other extremity, situated on the side of the hoist, is equipped with a device permitting its axial displacement and is associated with a force sensor and with a displacement sensor.

This mounting makes it possible to perform the following various types of tests:

- A constant force is applied to the specimen-forming component, after which the change in length is measured as a function of an applied change in the temperature.
- A length change is applied to the specimen-forming component, after which the force developed by the specimen during a temperature change is measured.
- The temperature of the specimen-forming component is fixed, after which the force necessary to deform it, in tension or in compression, is measured.

So as to apply a deformation or a deformation rate to a specimen-forming component, the extremity of the rod situated on the side opposite the component to be monitored is fixed by the intermediary of a force sensor to a screw-nut device, of which one of the components is associated with the support for the force sensor and of which the other component is associated with the support frame, so as to convert an applied rotation into a translational movement.

In the case where the machine is equipped for monitoring two components disposed parallel to each other, the two force sensors with which they are associated are mounted on a single plate moveable in translation in a controlled manner, which ensures that the same deformation is applied to both specimens.

The reliability of the measurements is advantageously increased by using a differential operation. For this purpose, two components are disposed in the machine, one serving as a reference and the other being for characterizing.

The force sensors used are for example of the strain gage type.

Each rod, of which one extremity is associated with a specimen-forming component, is equipped, in the vicinity of its extremity situated outside the enclosure, with a strip which is perpendicular to it and which carries the moveable portion of a displacement sensor.

Advantageously, each displacement sensor is of the magnetic type and reacts to the displacement of a soft iron core which is integral with the rod whose displacement is to be measured.

So as to prevent thermal loss from the enclosure, and to permit a reliable operation of the instrumentation despite the large temperature changes, the portion of the support frame traversing the outer casing, the insulating material and the wall of the vessel is tubular and mounted with joints in between seals, in the fixed tubular components traversing these components, this tubular portion itself comprising a tube for guiding each rod, in which the latter is mounted, with ball sleeves in between a thermal insulation being provided between the rod and the sleeves so as to protect the latter from the extreme temperatures which can prevail inside the enclosure.

As the instruments are disposed outside the enclosure they are not subjected to large temperature changes.

Advantageously, the machine is equipped, on the side of the vessel diametrically opposite that comprising the instrumentation for measuring the deformations, with a device for measuring acoustic emission mounted on the stirrup carrying the component or components to be monitored, by the intermediary of a support frame comprising, in its zone traversing the wall of the vessel, the thermal insulation and the casing, a tubular portion mounted with seals in between, in the fixed tubular components traversing these components.

For precision of the measurement and reliability reasons, the acoustic emission sensor is mounted outside the enclosure containing the component to be monitored, the ultrasonic waves being guided from the component to the sensor by a waveguide bearing under an adjustable tensile force, on the one hand, on the component and, on the other hand, on the sensor, means being provided for producing a mounting decoupling, on the one hand, the waveguide from the support frame of the machine in order to be free of extraneous vibrations and permitting, on the other hand, an independent adjustment of the pressures between waveguide and sensor and waveguide and component.

The acoustic emission sensor is, for example, a piezoelectric sensor, of the resonant or wide band type.

The acoustic emission measurements permit measurements of the magnitude of the dynamic phenomena related to rupture, but also to plastic deformations and to the martensitic transformation. It is thus possible to determine, by this measurement, the dynamics of the martensitic transformation This enables the history of the alloy to be monitored in relation to the martensitic transformation and therefore the future behavior of the alloy to be predicted.

In order to measure the resistivity, four electrical contacts are made on the component by spot welding. This measurement enables the transformation to be followed while determining, as the latter progresses, the percentage transformed.

So as to measure the temperature of the component to be monitored, continuously, a thermocouple is welded to the specimen by spot welding.

BRIEF DESCRIPTION OF THE DRAWING

In any case, the invention will be well understood with the aid of the description which follows, with reference to the attached diagrammatic drawing, representing by non-limiting example an embodiment of this machine.

DESCRIPTION OF THE PREFERRED EMBODIMENTS

Figure 1:
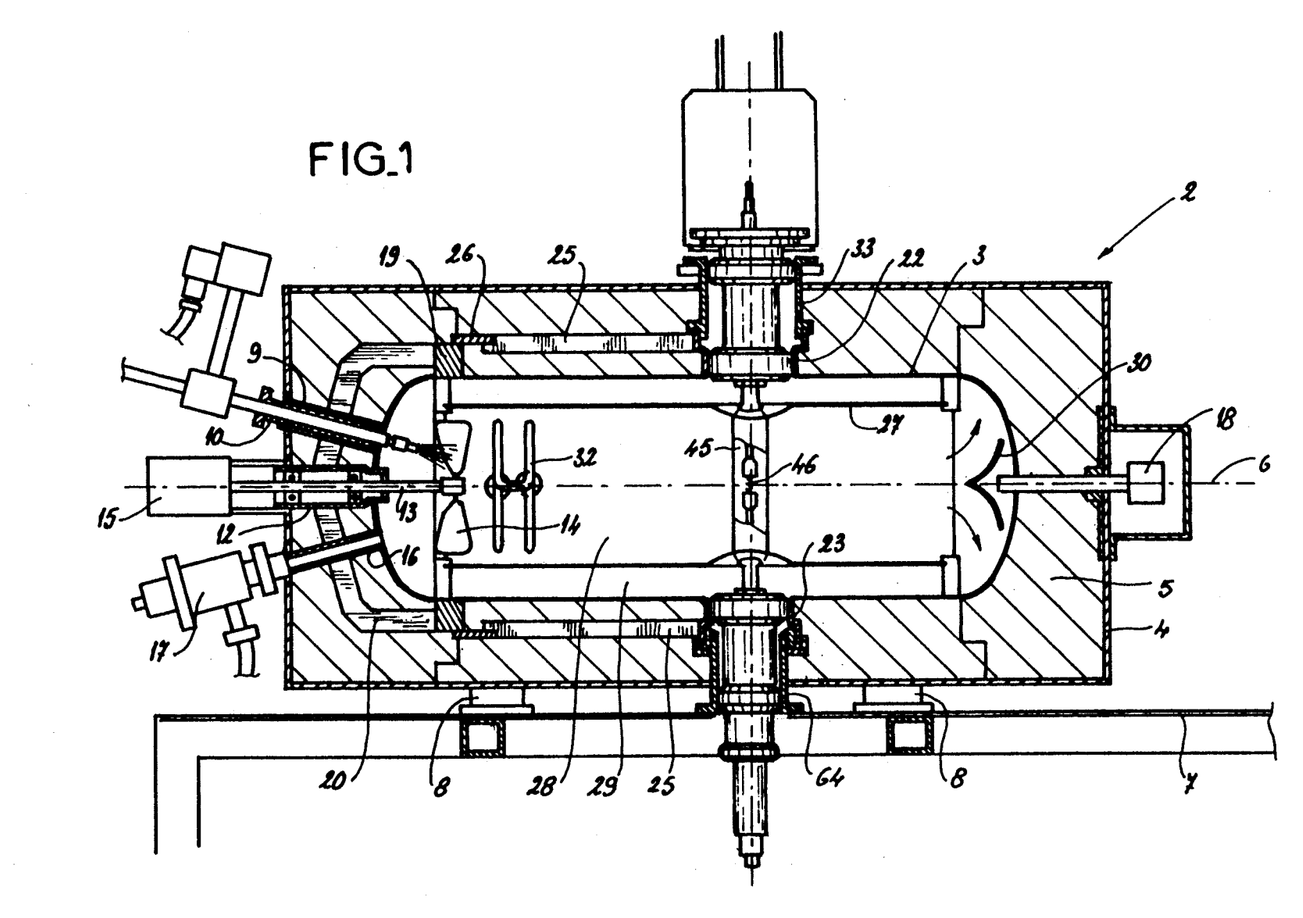
FIG. 1 is a view, in partial longitudinal cross section, relating to the thermal enclosure.

The machine according to the invention essentially comprises a thermal enclosure 2 making it possible to insulate the elements to be monitored from external influence and to subject them to temperatures varying over a range between approximately −150° C. and +300° C., whilst providing a good temperature uniformity around the components. This thermal enclosure comprises a stainless steel vessel 3 comprising a cylindrical-shaped central portion closed at its extremities by ends curved outwardly. This vessel 3 is mounted inside a casing 4, likewise made of stainless steel, constituted for example by two half-shells assembled together, with a rigid insulating material 5 in between. In practice, the axis 6 of the thermal enclosure is horizontal and the inner vessel 3 rests on the insulating component. The outer casing is in turn mounted on a support 7 by the intermediary of feet 8. To one of the ends of the vessel are fixed three tubular inlets, which traverse, loosely, the insulating component, and the outer casing. This is a tubular inlet 9 for the passage of a tube 10 supplying cryogenic fluid such as liquid nitrogen, an axial tube 12 permitting the passage of a drive shaft 13 of a fan 14 from a motor 15 and a tubular inlet 16 permitting the passage of a pipe at the end of which is mounted, outside the casing 4, a valve 17 providing the regulation of the pressure inside the vessel. At the other extremity of the vessel, emerges, into the end of the latter, a safety valve 18.

Figure 2:
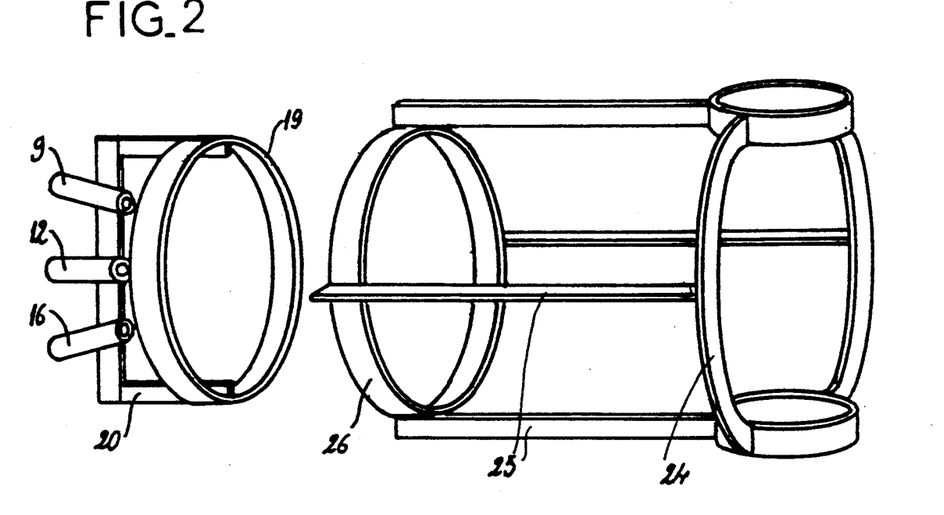
FIG. 2 is an exploded and larger-scale view, in perspective, of the structure associated with the thermal enclosure, intended for carrying the principal components of the instrumentation.

The vessel 3 is equipped, at its extremity comprising the tubular inlets 9, 12, 16, with a ring 19 which is peripheral, fixed to the cylindrical portion in the vicinity of the end in question and carrying a stirrup 20 to which are fixed the tubular inlets 9, 12, 16. Furthermore, the vessel comprises two diametrically opposed openings serving for the passage of a specimen holder and of the measurement instrumentation. These two openings are delimited by collars 22 and 23. These collars 22 and 23 are integral with a ring 24 connected by means of four longitudinal bars 25 to a ring 26 which is mounted in a fitted manner and with the capability for sliding axially over the ring 19 carrying the stirrup 20 as shown in FIG. 2. This structure makes it possible to link the various components of the machine in a closed manner whilst permitting the accommodation of the thermal expansions of the vessel 3, by the sliding of the two rings 19 and 26 over each other. It should be noted that this assembly possesses only one point fixed in relation to the outside constituted by the passage for the instrumentation, which permits a clear space for all the other parts.

Furthermore, the vessel comprises a cylindrical wall 27 made of thin metal sheet, situated parallel to the cylindrical wall delimiting the vessel and inside the latter. This cylindrical portion 27 extends over the major portion of the length of the cylindrical portion of the vessel 3. This cylindrical metal sheet 27 delimits, with the vessel, an inner and central zone 28 and an outer annular zone 29. The fan 14 faces the central zone 28, this zone containing the components to be monitored and providing the channeling of the flux of gaseous fluid such as air from the fan, from the left towards the right in the drawing, this flux of air being channeled at the right hand extremity of the vessel, with the aid of a separator 30, towards the outside, and returning via the annular volume 29 in the left hand portion of the vessel. A heating resistance element 32 is disposed downstream of the fan 14 in the displacement direction of the flux of air. This fan improves the heat transfer between the heating resistance element and the air of the enclosure, the mixing of nitrogen and air and, especially, the evaporation of the liquid nitrogen as well as the heat transfer between the ambient air of the enclosure and the components to be monitored.

A monitoring and control unit, not shown in the drawing, provides the regulation of the temperature by acting on the nitrogen supply and on the electrical power supply to the resistance element 32. Furthermore, a computer records and processes all the data during the period of monitoring.

Figure 3:
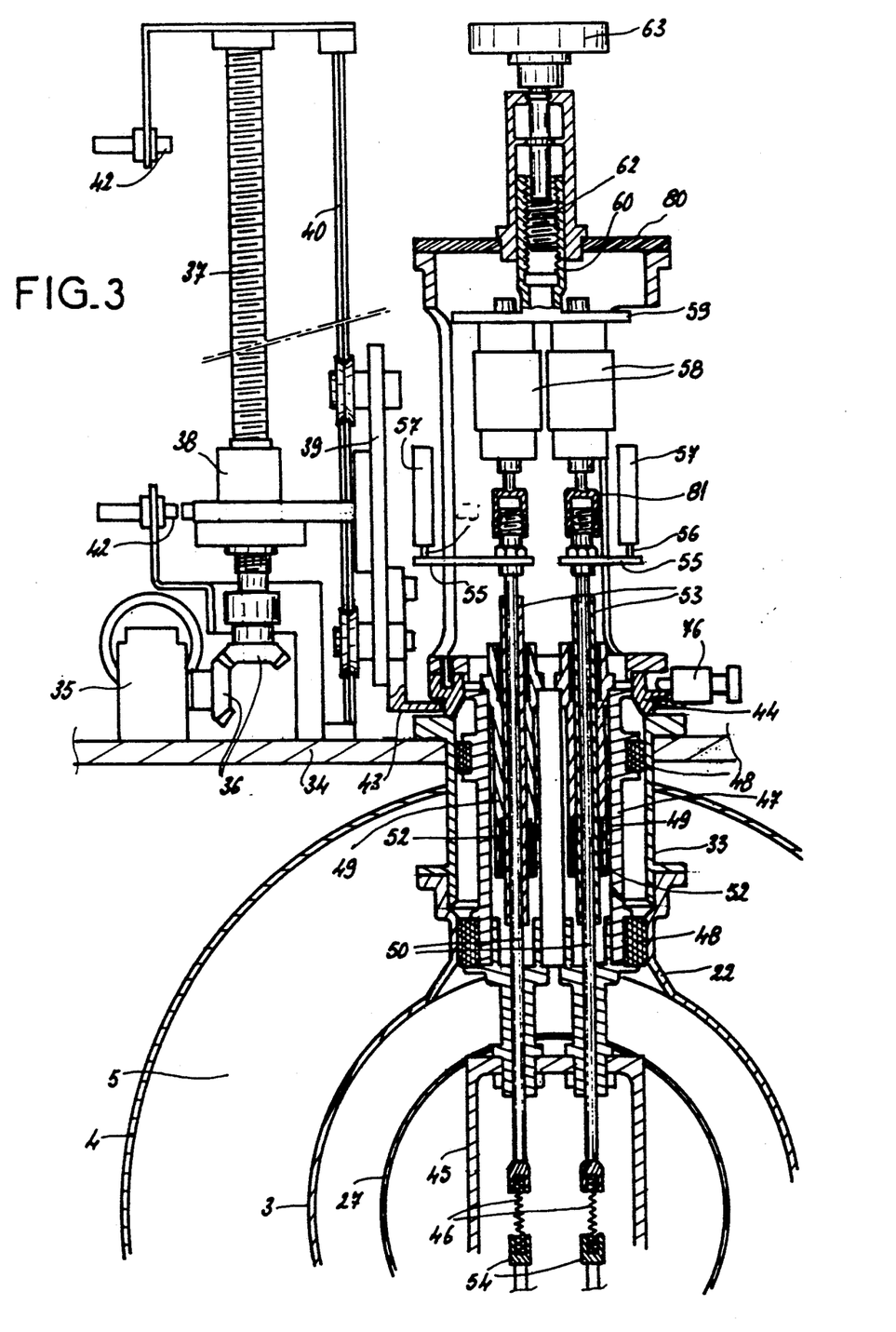
FIG. 3 is a view, in cross section in a plane perpendicular to the axis of the thermal vessel, representing the system for applying stress and for mechanical measurement of the deformations.

As shown in FIGS. 1 and 3, the collar 22 delimiting an opening emerging in the vessel 3, is integral with a tubular portion 33 which extends it upwards, and which traverses the insulation 5 and the outer casing 4. The extremity of the tubular part 33 carries a platform 34 on which is mounted a hoisting device intended for moving the instrumentation and the components to be monitored during their installation in the vessel and their withdrawal out of the latter. This hoisting device comprises a gear motor 35 which drives, by the intermediary of two sprockets 36, an endless screw 37 which is engaged in a nut 38 integral with a carriage 39 guided on rails 40. The screw 37 and the rails 40 are oriented parallel to the axis of the tubular portion 33. This hoisting device is equipped with two inductive sensors 42, intended for stopping the motor 35 at the end of the travel up and the travel down.

As shown in FIG. 3, the carriage 39 is equipped with a zone 43 for securing it to the support frame 44 carrying the instrumentation.

This support frame 44 is equipped with a stirrup 45 which, in the measurement position, is inside the vessel 3 and serves for the mounting of the two components 46 to be monitored.

As shown in FIG. 3, the support frame comprises a portion 47, which is tubular and whose periphery is equipped with seals 48 intended for sealing around the components 22, 33 traversing the walls of the vessel 3, the insulation 5 and the outer shell 4. Inside this tubular portion 47 are mounted two tubes 49 each serving for the passage of a rod 50 and which are capable of guiding each of the latter with the aid of two ball sleeves 52. Each rod 50 is mounted in the ball sleeves 52 with a layer 53 of a thermally insulating material in between.

The components 46 to be monitored, wires or springs, bear or are fixed by their base, against a fixed stop 54 integral with the support frame of the machine and, by their other extremity, to an extremity of a rod 50. In order to fix these, it is advisable not to affect the heat exchange between the heat transferring fluid and the specimen and, if this is a spring, to prohibit any movement of the latter without, however, crushing it.

The free extremity of each rod 50 is situated outside the thermal enclosure. At its free extremity, each rod 50 comprises a strip 55 which is perpendicular to it, this strip 55 itself carrying a finger 56 made of soft iron constituting the moveable component of a magnetic displacement sensor 57. The extremity of the rod 50 is also associated, detachably, with a force sensor 58 of the strain gage type. The two force sensors 58 of the two rods 50 are fixed to the same plate 59 which is equipped with a nut 60 in which is engaged a screw 62 which can be actuated by an operating knob 63 and is mounted, free in terms of rotation but locked in terms of translational movement, on the support frame. In a diametrically opposed position, the thermal enclosure is equipped with a device for measuring acoustic emission., fixed to the stirrup 45, and traversing the wall of the vessel on the one hand, but also the thermal insulation and the outer wall.

Figure 4:
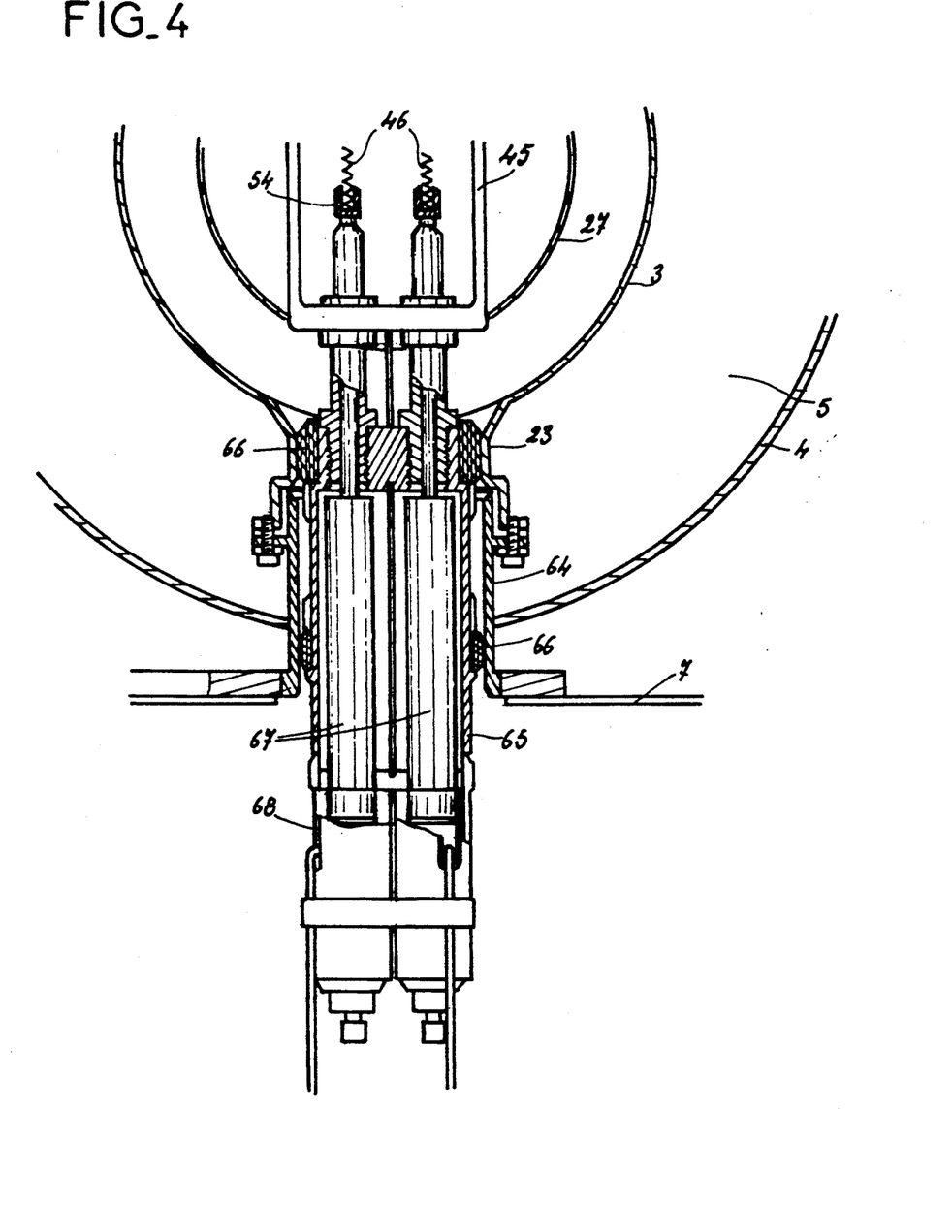
FIG. 4 is a view complementary to FIG. 3, in cross section in the same plane transverse to the thermal enclosure, showing a device for measuring the acoustic emission.

For this purpose, a tubular portion 64, which traverses the rigid insulation 5 and the outer casing 4 and is centered on the support 7, is fixed to the collar 23 delimiting the opening made in the lower portion of the vessel. The collar 23 and the tubular component 64 are traversed by a tubular portion 65 which is integral with the stirrup 45 and is mounted, with seals 48 in between, against the collar 23 and the tubular portion 64.

The device for measuring acoustic emission comprises, for each component, a waveguide 67 which bears, in a manner not shown in the drawing, directly against the component 46 to be monitored, without any other contact and without, however, affecting the fixing of the latter against the component 54 provided for this purpose. This waveguide extends to the outside of the outer casing 4 and bears against an acoustic emission sensor 68.

Provision is made for means enabling pressure to be applied to the waveguide 67, in an adjustable manner, against the component 46 and means for applying pressure to the acoustic emission sensor 68 against the waveguide 67, these means regulating the two pressures independently.

It is clear from this structure that if the specimen is placed in an enclosure capable of subjecting it to very large temperature changes, for example in a range from $-150°$ C. to $+300°$ C., all the instruments are situated outside this enclosure and are therefore not affected by the significant changes in temperature.

The use of this machine is the following one. In order to install components to be monitored in their respective support, the procedure is to actuate the motor 35 in order to raise the instrumentation until the stirrup 45 is outside the enclosure. Before fixing the components to their respective supports, the procedure is to weld the thermocouple and the four connections necessary for measuring the resistivity. The operator then fixes each component 46 on the one hand by its base at the level of the part 54 on the support frame and at its extremity to a rod 50.

Then the procedure is to connect the thermocouple to the measurement apparatus and to connect up the four connection wires intended for the resistivity measurement.

With the elements 46 in place, the motor 35 is switched on in a direction of downward displacement of the carriage 39, which corresponds to the insertion of the stirrup 45 inside the vessel. This displacement is performed until the end of the travel down of the carriage, a position in which the support frame 44 bears against the upper edge of the tubular part 33. As previously, the angular positioning of the component holder with regard to the support frame has been carried out by engagement of a finger 76 inside a corresponding recess provided in the support frame The operator verifies that the forces applied to the components are zero, and then adjusts the contact forces between each waveguide 67 and the corresponding component 46 and between each waveguide 67 and the corresponding sensor 68.

It is then possible to perform the desired operations.

A typical measurement consists in applying a deformation to the components 46 and in measuring the force necessary for maintaining this deformation during a temperature change. It is the mounting of the tension-compression type which is used in that case. The components are brought to the initial temperature, after which the desired deformation is fixed with the aid of the screw 62 for applying load. It is then possible to start executing a cycle for changing the temperature.

Another type of measurement consists in applying a temperature to the components and then subjecting them to tension or compression tests. In this case, the components are brought to the test temperature while not being subjected to any stress. Then, by actuating the screw 63, they are progressively deformed up to a maximum value. During this deformation, the procedure is to record the acoustic emission, the temperature, the resistivity, the deformation force and the deformation. When the maximum value of deformation is reached, the load exerted on the components is reduced until obtaining a zero force applied . It is possible to start another test, or to stop the operations or to link up several of the abovementioned operations in whatever order.

When the test is completed, the thermal enclosure is brought back to ambient temperature and the components are removed by extraction from the central vessel by the intermediary of the hoisting device and, especially, of the motor 35. It is then possible to unweld the wires for measuring resistivity and to disconnect the thermocouple. The monitored components are demounted and other components may be installed in their place.

Figure 5:
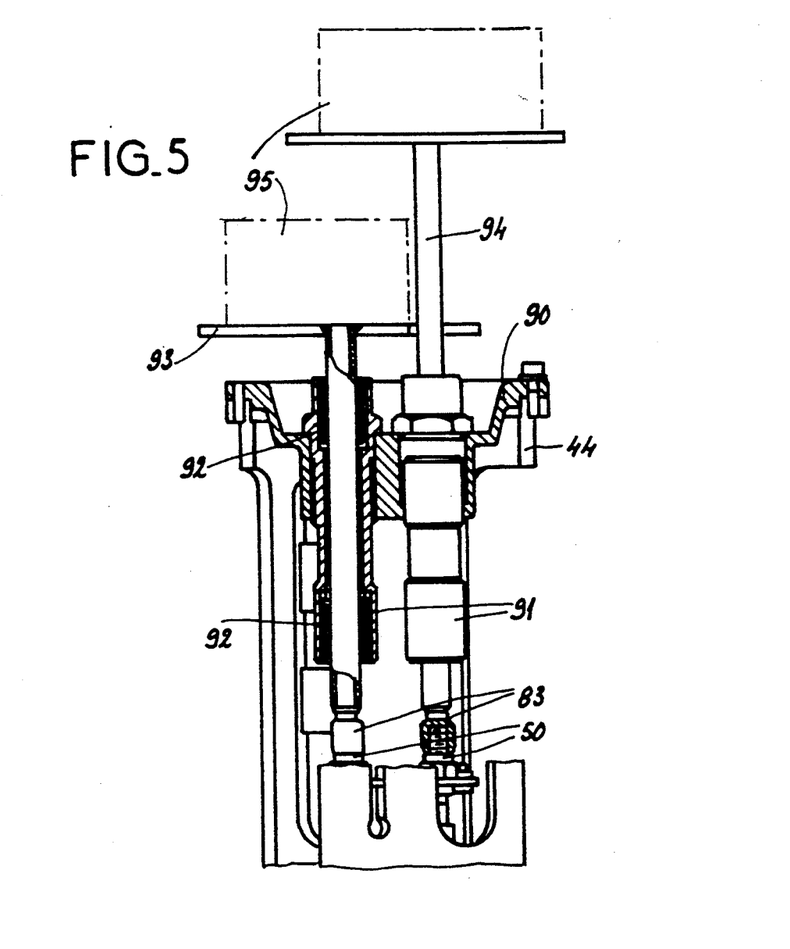
FIG. 5 is a detailed view showing a mounting adapted for exerting a constant force on the components to be analyzed.

If it is desired to apply a constant force to the components and to measure the length change of the components as a function of a temperature change, it is advisable to use the mounting attachment an embodiment of which is given by way of example in FIG. 5. This mounting is attached to the support frame of the instrumentation and replaces the parts 58 to 63 and 80–81. The demounting of these parts is undertaken by decoupling the rods 50 from the sensors 58, by unscrewing the nuts 81 and by disconnecting the part 80 from the support frame 44 by removing the screws. The constant force mounting may then be positioned by fixing the part 90 to the support frame 44 instead of and in place of the part 80, by screwing and by coupling the rods 50 to the platens 93 and 94 with the aid of nuts 83 which are identical to the screws 81.

When the mounting is in place, the components to be monitored not being subjected to any stress are brought to the temperature for starting the tests. The weights (95) of known masses are then placed on the platens 93 and 94. Thus these platens guided in translational movement by the ball guides 92 bear on the components by the intermediary of the rods 50, subjecting the components to a constant compressive force regardless of the temperature and the deformation of the components.

The temperature cycle having been programmed is then initiated by the operator. Simultaneously it is appropriate to actuate the computer in order to start the acquisition of the acoustic emission, the resistivity, the temperature and the displacement.

As is clear from the above, the invention greatly improves the current technique by providing a machine permitting the transformation of a component to be monitored whilst measuring several parameters, it being possible for this monitoring to be carried out over a very wide temperature range, without deterioration of the instrumentation, and completely reliably by virtue of the expansion capabilities of the components which are subjected to the temperature.

As is obvious, the invention is not limited to the single embodiment of this machine, described hereinabove by way of example, but on the contrary it embraces all alternative forms.

We claim:

1. A machine for monitoring the characteristics of materials having a phase transformation, comprising:
    a thermally insulated enclosure having a longitudinal axis;
    a temperature changing source for changing the temperature within the enclosure;
    a device for making the temperature within the enclosure uniform;
    a specimen holder disposed inside the enclosure;
    measurement instrumentation associated with the specimen holder; and
    mounting means uncoupled from the enclosure for mounting the specimen holder and the measurement instrumentation fixed relative to the enclosure, with the specimen holder being movable transverse to the longitudinal axis of the enclosure, for permitting thermal expansion of the thermally insulated enclosure relative to and independent of the mounting means due to temperature differences.

2. A machine for monitoring the characteristics of materials having a phase transformation, comprising:
    a thermally insulated enclosure;
    a temperature changing source for changing the temperature within the enclosure;
    a device for making the temperature within the enclosure uniform;
    a specimen holder disposed inside the enclosure;
    measurement instrumentation associated with the specimen holder; and
    mounting means uncoupled from the enclosure for mounting the specimen holder and the measurement instrumentation fixed relative to the enclosure, for permitting thermal expansion of the thermally insulated enclosure relative to and independent of the mounting means due to temperature differences; and
    wherein the thermally insulated enclosure comprises a metal casing; a steel vessel of generally cylindrical shape housed inside the metal casing; rigid insulating material disposed between the casing and the vessel; the vessel having two outwardly curved opposed ends, one of the ends of the vessel having three tubular inlets transversing the insulation and the metal casing, which inlets are adapted respectively, for supplying cryogenic fluid, for the passage of a drive shaft of a fan for circulating gaseous fluid inside the enclosure and making the temperature uniform, and for regulating pressure within the vessel, a first ring fixed to a cylindrical portion of the vessel in the vicinity of said one end, a stirrup-shaped member mounted on the first ring, said tubular inlets being mounted on the stirrup-shaped member and, at lease one radial opening for the passage of the specimen holder into the vessel, said radial opening being delimited by a collar; a second ring surrounding the vessel, said collar being integral with said second ring; a third ring, said third ring being mounted on the vessel in a fitted manner and with the capability for sliding axially over the first ring carrying the stirrup-shaped member, and a plurality of longitudinal bars connecting the third ring to the second ring.

3. The machine as claimed in claim 2, further comprising a support; said casing resting on the support whereby the vessel has a horizontal axis; a second radial opening extending through the casing and the vessel for the passage of the measurement instrumentation, said second radial opening being diametrically aligned with said first radial opening and fixed to the support.

4. The machine as claimed in claim 2, wherein the thermally insulated enclosure comprises a cylindrical metal sheet wall, said cylindrical wall extending in a cylindrical portion of the vessel, and delimiting a central zone and an annular zone; openings in the cylindrical wall for the passage of the specimens and the measurement instrumentation, a fan disposed adjacent one of the end walls of the vessel, said fan facing the central zone and an end of the vessel opposite to the fan; a flux separator in opposed relation to the fan for encouraging the return of the air via the annular zone and wherein the temperature changing source comprises a heating element disposed in the central zone, downstream from the fan, in the outflow direction of the flux of air from the fan.

5. The machine as claimed in claim 2, wherein said collar faces upwards and includes a tubular portion extending from the collar and traversing the insulation and the metal casing; a platform mounted on the tubular portion outside the metal casing; a hoisting device mounted on the platform for moving the instrumentation and the specimens during their installation in the vessel and their withdrawal out of the vessel.

6. The machine as claimed in claim 5, wherein the hoisting device comprises:
    a gear motor;
    a screw driven by the gear motor and having an axis parallel to that of the direction of movement of the measurement instrumentation;
    a nut mounted on the screw;
    a carriage, the nut being integral with the carriage;
    rails parallel to the screw for guiding the carriage, said carriage being locked to a support frame carrying the measurement instrumentation, whereby translational movement of the carriage is imparted to the support frame; and sensors for controlling the gear motor at an upper end of travel and a lower end of travel of the carriage.

7. The machine as claimed in claim 6, wherein the support frame carrying the measurement instrumentation includes a second stirrup positionable in a measurement position inside the vessel, said second stirrup including mounting means for mounting a component to be monitored, said mounting means including means for engaging a first extremity of the component, said mounting means including a rod mounted on the second stirrup, said rod having a first end portion for engaging the first extremity of the component; said rod having a generally radial orientation in relation to the enclosure; said rod being mounted in a sliding manner in relation to the support frame, said rod having a second end situated on the side of the hoist; a device for axially displacing the rod; a force sensor associated with the rod; and a displacement sensor associated with the rod.

8. The machine as claimed in claim 7, wherein the second end of the rod is joined by the force sensor to a screw-nut device, having first and second relatively movable elements; the first element engaging the force sensor and the second element engaging the support frame, said screw nut device converting an applied rotation into a translational movement.

9. The machine as claimed in claim 8, wherein the second stirrup includes means for mounting two components disposed parallel to each other; a second force sensor; a single plate moveable in translation in a controlled manner on the support frame, said first and second force sensors being mounted on the plate.

10. The machine as claimed in claim 7, wherein the second end of the rod is situated outside the insulated enclosure, a perpendicular strip is mounted on said second end of the rod and said strip carries a moveable portion of the displacement sensor.

11. The machine as claimed in claim 10, wherein the displacement sensor is of a magnetic type and wherein the moveable portion of the displacement sensor is a soft iron core which is integral with the rod to measure the displacement of the rod.

12. The machine as claimed in claim 7, wherein a portion of the support frame extends between the outer casing, the insulating material and the wall of the vessel; said portion of the support frame being tubular; seals mounted on the tubular portion; a tube mounted on the tubular portion for guiding said rod, ball sleeves in the tube for slidably mounting the rod in the tube, and thermal insulation disposed between the rod and the ball sleeves.

13. The machine as claimed in claim 7, further comprising:

a device for measuring acoustic emissions; said acoustic emissions measuring device being mounted on the second stirrup diametrically opposite to said at least one radial opening, a second support frame for supporting the acoustic emission measuring device, said second support frame having a second tubular portion traversing the wall of the vessel, the thermal insulation and the casing; and seals on the tubular portion of the second support frame for sealing with the second tubular component traversing the vessel, the thermal insulation and the casing.

14. The machine as claimed in claim 13, wherein the acoustic emission measuring device is mounted outside the enclosure containing the component to be monitored, a waveguide is mounted on the second support frame for guiding ultrasonic waves from the component to be monitored to the acoustic emission measuring device; and mounting means are provided for decoupling the waveguide from the second support frame to isolate the waveguide from extraneous vibrations and to adjust independently the bearing force of the waveguide on the component to be monitored and on the acoustic emission measuring device.

15. The machine as claimed in claim 7, wherein the second stirrup includes means for mounting and measuring two components; and means for taking differential measurements of the electrical resistivity, the acoustic emission and the deformation of one of the components in comparison with the other component.

* * * * *